United States Patent
Coffee (10) Patent No.: US 6,318,640 B1
(45) Date of Patent: Nov. 20, 2001

(54) DISPENSING DEVICE

(75) Inventor: Ronald Alan Coffee, Haslemere (GB)

(73) Assignee: Electrosols, Ltd., Surrey (GB)

( * ) Notice: Subject to any disclaimer, the term of this patent is extended or adjusted under 35 U.S.C. 154(b) by 0 days.

(21) Appl. No.: 09/535,518

(22) Filed: Mar. 24, 2000

Related U.S. Application Data (63) Continuation of application No. 08/835,676, filed on Apr. 10, 1997, now Pat. No. 6,105,877, which is a continuation of application No. 08/456,432, filed on Jun. 1, 1995, now abandoned.

(30) Foreign Application Priority Data

Dec. 1, 1992 (GB) .................................................. 9225098

(51) Int. Cl.$^7$ ................................ B05B 5/025; B05B 5/00
(52) U.S. Cl. .............................. 239/3; 239/690; 239/695; 239/696; 239/102.2; 361/227; 128/204.21
(58) Field of Search ............................. 239/3, 690, 695, 239/696, 708, 102.2; 128/203.12, 203.14, 204.13, 204.21; 361/227, 228

(56) References Cited

U.S. PATENT DOCUMENTS

| | | |
|---|---|---|
| 2,723,646 | 11/1955 | Ransberg . |
| 2,945,443 | 7/1960 | Aver et al. . |
| 3,096,762 | 7/1963 | Winchell . |

(List continued on next page.)

FOREIGN PATENT DOCUMENTS

| | | |
|---|---|---|
| P 2008769 | 9/1970 | (DE) . |
| 4106564A1 | 9/1992 | (DE) . |
| 005035A | 10/1979 | (EP) . |
| 0029301A1 | 5/1981 | (EP) . |
| 0120 633 A2 | 10/1984 | (EP) . |
| 0234841A | 9/1987 | (EP) . |
| 0234842 | 9/1987 | (EP) . |
| 02050164A3 | 12/1987 | (EP) . |
| 0250102 A | 12/1987 | (EP) . |
| 052393A1 | 7/1992 | (EP) . |
| 0523963A1 | 7/1992 | (EP) . |
| 0523962A1 | 1/1993 | (EP) . |
| 523964A1 | 1/1993 | (EP) . |
| 1297993 | 11/1972 | (GB) . |
| 1569707 | 6/1980 | (GB) . |
| 2018627B | 4/1982 | (GB) . |
| 2 128 900 A | 5/1984 | (GB) . |
| 0 102 713 B1 | 9/1987 | (GB) . |
| 2 201 873 A | 9/1988 | (GB) . |
| 1005939A | 6/1981 | (SU) . |
| WO 91/07232 | 5/1991 | (WO) . |
| WO 92/15339 | 9/1992 | (WO) . |
| WO 93/00937 | 4/1993 | (WO) . |
| WO 93/06937 | 4/1993 | (WO) . |
| WO 9412285 | 6/1994 | (WO) . |
| WO94 13266A | 6/1994 | (WO) . |
| WO 94 14543A | 7/1994 | (WO) . |
| WO 95 26235A | 10/1995 | (WO) . |
| WO 9526235 | 10/1995 | (WO) . |
| WO 9532807 | 12/1995 | (WO) . |
| WO 9907478 | 2/1999 | (WO) . |

*Primary Examiner*—David A. Scherbel
(74) *Attorney, Agent, or Firm*—Cobrin & Gittes (57) ABSTRACT

A comminuting liquid device, a medicament delivery device, an inhaler, a method of providing droplets for delivery to the respiratory tract, a pocket-sized dispenser, and a method of mixing liquids by droplet coalescence. Liquids are subjected to electrical potentials to produce electrically charged droplets for delivery to the upper respiratory tract.

19 Claims, 4 Drawing Sheets

U.S. PATENT DOCUMENTS

| | | |
|---|---|---|
| 3,131,131 | 4/1964 | Wehner . |
| 3,232,292 | 2/1966 | Scheaefer . |
| 3,456,646 | 7/1969 | Phillips et al. . |
| 3,837,573 | 9/1974 | Wagner . |
| 3,897,905 | 8/1975 | Tadewald . |
| 3,930,061 | 12/1975 | Scharfenberger . |
| 3,958,959 | 5/1976 | Cohen et al. . |
| 4,043,331 | 8/1977 | Martin et al. . |
| 4,044,404 | 8/1977 | Martin et al. . |
| 4,073,002 | 2/1978 | Sickles et al. . |
| 4,150,644 | 4/1979 | Masaki et al. . |
| 4,186,886 | 2/1980 | Sickles . |
| 4,198,781 | 4/1980 | Dykes . |
| 4,203,398 | 5/1980 | Maruoka . |
| 4,266,721 | 5/1981 | Sickels . |
| 4,356,528 | 10/1982 | Coffee . |
| 4,380,786 | 4/1983 | Kelly . |
| 4,439,980 | 4/1984 | Biblarz et al. . |
| 4,467,961 | 8/1984 | Coffee et al. . |
| 4,476,515 | 10/1984 | Coffee . |
| 4,508,265 | 4/1985 | Jido . |
| 4,509,694 | 4/1985 | Inculet et al. . |
| 4,549,243 | 10/1985 | Owen et al. . |
| 4,565,736 | 1/1986 | Stein et al. . |
| 4,657,793 | 4/1987 | Fisher . |
| 4,659,012 | 4/1987 | Coffee . |
| 4,671,289 | 6/1987 | Wilp . |
| 4,703,891 | 11/1987 | Jackson et al. . |
| 4,735,364 | 4/1988 | Marchant . |
| 4,748,043 | 5/1988 | Seaver et al. . |
| 4,749,125 | 6/1988 | Escallon et al. . |
| 4,779,515 | 10/1988 | Michalchik . |
| 4,801,086 | 1/1989 | Noakes . |
| 4,830,872 | 5/1989 | Grenfell . |
| 4,846,407 | 7/1989 | Coffee et al. . |
| 4,962,885 | 10/1990 | Coffee . |
| 4,979,680 | 12/1990 | Baach et al. . |
| 5,044,564 | 9/1991 | Sickles . |
| 5,086,972 | 2/1992 | Chang et al. . |
| 5,115,971 | 5/1992 | Greenspan et al. . |
| 5,180,288 | 1/1993 | Richter et al. . |
| 5,222,663 | 6/1993 | Noakes et al. . |
| 5,267,555 | 12/1993 | Pajalich . |
| 5,381,789 | 1/1995 | Marquardt . |
| 5,402,945 | 4/1995 | Swanson . |
| 5,409,162 | 4/1995 | Sickles . |
| 5,483,953 | 1/1996 | Cooper . |
| 5,655,517 | 8/1997 | Coffee . |
| 6,105,877 * | 8/2000 | Coffee ........................... 239/3 |

\* cited by examiner

DISPENSING DEVICE

This is a continuation of U.S. Application Ser. No. 08/835,676 filed Apr. 10, 1997, now granted as U.S. Pat. No. 6,105,877 on Aug. 22, 2000, which in turn is a continuation of U.S. Application Ser. No. 08/456,432 filed Jun. 1, 1995, now abandoned, which is a national phase entry under 35 USC §371 of PCT/GB30/02443, filed Nov. 26, 1993.

The invention relates to a dispensing device for comminuting a liquid, means for supplying liquid for use in such device and the use of such a device, in particular, in medicine.

Dispensing devices are known which produce a finely divided spray of liquid droplets by electrostatic means(more properly referred to as 'electrohydrodynamic' means). Electrohydrodynamic sprayers have found use in many areas of industry, especially in agriculture for crop spraying, paint spraying in the automotive industry and also in medicine for the administration of medicaments by inhalation.

The droplet spray in such devices is generated by applying an electric field to a liquid located at a spray head or spray edge. The potential of the electric field is sufficiently high to provide comminution of electrically charged liquid droplets from the spray head. The electrical charge on the droplets prevents them from coagulating via mutual repulsion.

United Kingdom patent number 1569707 describes an electrohydrodynamic spray device principally for use in crop spraying. An essential component of the GB 1569707 spray device is a field intensifying electrode, cited adjacent the spray head and maintained at the same potential as the spray head. The field intensifying electrode is not supplied with liquid In use it is stated to reduce the incidence of corona discharge which interfere with spray production and thereby allows lower electric field strengths to be used during spray generation.

U.S. Pat. No. 4,703,891 describes a crop spraying apparatus for spraying liquids from a vehicle such as an aircraft or other airborne vehicle, having at least two sprayheads arranged to produce spray of positive charge at one sprayhead and negative charge at the other. The resulting charged sprays are then applied to the relevant crops.

In many circumstances it is desirable to partially or wholly remove the electric charge from droplet sprays produced by electrohydrodynamic comminution devices in a controlled manner. To date the principal method used to effect comminution discharge has required the use of a discharging electrode having a sharp or pointed edge and located downstream from the spray head. The discharging electrode produces a cloud of charged ions from the surrounding air having an opposite electrical charge of equal magnitude to that on the comminuted liquid spray. In use, the ion cloud is attracted towards, collides with and thereby neutralizes the liquid spray.

United Kingdom patent number 2018627B discloses an electrohydrodynamic spray device wherein the electric charge on the droplet spray is fully or partially removed by means of a discharge electrode. The UK 2018627B device is stated to provide discharged or partially discharged sprays for crop spraying purposes. European Patent number 0234842 discloses an electrohydrodynamic inhaler wherein the spray of charged droplets is similarly discharged by means of a discharge electrode. The droplets are discharged in order to facilitate droplet deposition into the respiratory tract as otherwise the electrically charged droplets would deposit onto the mouth and throat of the user.

A particular problem associated with the use of the sharp discharge electrode is that the highly mobile ion cloud from the discharge electrode often interferes with the commninution of the liquid spray. The inhaler device of EP 0234842 attempts to ameliorate the effects of the ion cloud at the spray head by using a neutral shield electrode located close to the spray head.

It is a primary feature of the present invention that a device for comminuting a liquid is provided, which corn minutes the liquid by electrohydrodynamic means and which produces a partially or fully electrically discharged comminution without the need for the sharp discharge electrode described above. The present device does not have the problems associated with the discharge electrode and hence it does not require the use of a neutral shield electrode.

Accordingly, there is provided a device for comminuting a liquid, which comprises at least two electrohydrodynamic comminution means arranged so that in use comminutions of opposing polarity are formed which are substantially admixed after formation.

The electrohydrodynamic comminution means may be any conventional electrohydrodynanic comminution means, for example those described in the above mentioned patent specifications.

Suitably, each comminution means comprises a comminution site, generally being a surface or edge, from which the liquid comminution is produced.

A preferred conmminution surface or edge is provided by a thin capillary tube, a nozzle or a slot defined by two parallel plates. However any comminution surface or edge described in the above mentioned patent specifications may be used.

The device generally comprises an even number of comminution means but this is not essential, the key factors are that at least two of the comminution means provide comminutions of opposing polarity and that the comminutions produced are ananged to substantially admix Suitably, the device comprises 2,4 or 6 comminution means, however higher numbers can be used as required. An example of a device is that which has 2 comminution means. An example of a device is that which has 6 comminution means.

Suitably, each comminution means comprises a means for supplying liquid to the comminution site.

Appropriate means for supplying liquid to the comminution site include mechanical, electrical or electronic powered means such as pumps which ar capable of providing the required flow rate of liquid to the comminution site.

The comminution means of the invention can be used with a large range of flow rates, but generally operates with flow rates in the range of between 0.1 to 500 $\mu$L per second, such as 0.5 to 5 $\mu$L per second, especially for inhaled administration, or 10 to 200 $\mu$L per second, especially for agricultural use.

A suitable means for supplying the liquid includes a syringe pump or an electrically powered pump as described in EP 0029301.

It will be appreciated from the foregoing that the comminution means generally comprises a comminution site, a means for supplying a liquid to the comminution site and a means for electrically charging the comminution site to an electric potential sufficient to comminute the liquid in use.

Accordingly, in one particular aspect of the invention there is provided a device for comnrinuting a liquid, which comprises at least two electrohydrodynamic comminution means each comprising a comminution site, a means for supplying a liquid to the comminution site and a means for electrically charging the comminution site to an electric potential sufficient to comminute the liquid in use, wherein the comminution means are arranged so that in use comminutions of opposing polarity are formed which are then substantially admixed.

Suitably, each comminution means comprises a means for electrically charging the said comminution site to a potential sufficient to provide comminution of the liquid, the potential usually being of the order of 1–20 kilovolts.

The means for electrically charging the said comminution site, such as a surface or edge, may be provided by any conventional high voltage generator having the approat output, one particularly convenient generator being a piezo-electric generator.

The piezoelectric material for the generator may be chosen from several types, such as barium tianate ceramic, or pvdf polymers, which generate significant high-voltage electric charge displacement upon being pressurized. The choice and capacity may be so chosen as to offer control of the degree of pumping and/or atomization when operated.

The required voltage for use is provided when the piezo-electric generators are squeezed, and again (with opposite polarity) when the piezo-electric generators are released from pressure.

The arangement by which the comminutions are admixed enables the net charge on the admixed comminution to be either essentially neural, positive or negative. Generally, the residual positive or negative charges are less than the positive or negative charge on any of the premixed comminutions.

The net residual charge on the admixed comminution may be fixed for any given device or the arrangement may be such that the net residual charge on the admixed comminution may be regulated in a controlled manner. Thus the device of the invention optionally comprises a means for regulating the electrical charge on a comminution produced from any of the comminution means prior to admixture.

Suitable means for regulating the electrical charge on a comminution may be provided by a variety of methods, such as by incorporating a means for regulating the charging means so as to provide variable voltage output and/or a means for regulating the means for supplying a liquid to the comminution site so as to vary the liquid flow rate to the comminution site.

Suitable arrangements of the comminution means which enable the comminutions produced to be admixed includes any arrangement wherein the comminution means are relatively located so as to enable the comminutions to substantially admix. Favourably, the comminution means are arranged so that the comminutions produced are directed to converge into a mixing zone. For example, when the device comprises two comminution means they may be angled towards each other so as produce comminutions which converge into the mixing zone. Or when the device comprises three or more comminution means, they may be arranged so that the comminutions are directed to converge radially into the mixing zone. Alternatively, the relative location of the comminution means may be arranged such that the mutual attraction of the comminutions produced is sufficient to allow substantial admixing, for example they may be in a mutually parallel manner.

It is envisaged that a liquid supply means may supply one or more of the comminution means of the invention.

Alternatively, a liquid supply means may supply only one comminution means.

From the foregoing it will be appreciated that it is an aspect of the present invention that comminuted sprays from different liquids may be mixed as required. Such liquids may be capable of providing a new product on admixture or they may comprise components which are so capable. The device may also be used to mix two liquids which are reactive components of a rapid chemical reaction. In each case the mixed droplets may then be applied as a spray, with a charge-to-mass ratio on the droplets that will be the residual after the two opposing charges have been used to coalesce the liquids.

Similarly, the present device may be used to mix components which are incompatible one with the other and which therefore are advantageously admixed at the point of use.

Suitable liquids include liquids comprising components useful for human or animal health care, such as medicaments for pharmaceutical or public health care use or medically useful compounds such as anesthetics.

Suitable liquids include liquids comprising components for agricultural use such as pesticides or biocides.

Suitable liquids include liquid cosmetic formulations.

Other suitable liquids include paints and inks. Also included are liquids for providing aromas.

Preferred liquids are pharmaceutically active liquids.

The comminution means of the dispenser provides liquid droplets within the range of from about 0.1 to about 500 microns in diameter More usually from 0.1 to 200 microns, such as 1.0 to 200 microns: Examples include droplets within the range of 5.0 to 100, 0.1 to 25, 0.5 to 10 or 10 to 20 microns. A favoured range for inhaled administration is 0.1 to 25 or 0.5 to 10 microns, especially for administration to the lower respiratory trat and 10 to 25 microns, especially for administration to the upper respiratory tract.

For a given liquid the diameter of the droplets can be controlled by varying the applied voltage and liquid flow rate using routine experimental procedures. Liquids having viscosities within the range of from 1 to 500 centipoise and resistivities in the range of from $10^2$–$10^8$ ohm m can be comminuted by the present device.

One favoured use of the device of the invention is for the dispensation of a comminuted liquid for inhalon.

Accordingly, in one preferred aspect of the invention there is provided a device for comminuting a liquid for inhalation, which comprises at least two electrohydrodynamic comminution means each comprising a comminution site, a means for supplying a liquid to the comminution site and a means for charging the comminution site to an electric potential sufficient to comminute the liquid in use, wherein the comminution means are arranged so that in use comminutions of opposing polarity are formed which are substantially admixed after formation.

The device of the invention may be adapted into any embodiment form which dispenses comminuted liquid for inhalation, for both medicinal and non-medicinal use.

Non-medicinal inhalation uses includes dispensing perfumes and aromas.

Preferably, the device is in the form of an inhaler, for the inhaled delivery of a medicament.

A preferred liquid is therefore a liquid medicament formulation adapted for inhaled administration.

Medicaments suitable for adaption for inhaled administration include those used for the treatment of disorders of the respiratory tract, such as reversible airways obstruction and asthma and those used in the treatment and/or prophylaxis of disorders associated with pulmonary hypertension and of disorders associated with right heart failure by inhaled delivery.

Since the charge-to-mass ratio of an electrohydrodynamic comminution may sometimes require optimization, to a value that may lie anywhere between the unadjusted value at the moment of comminution, and zero, the device of the invention may also be used to optimize droplet charges. For example, in order to apply a liquid containing a therapeutic agent to specific airways within a human lung, by inhalation, it would be highly beneficial if the droplet mass and charge could be independently controlled. This would give an unprecedented degree of control over the zone of deposition of the droplets within the lung.

For example in a two nozzle dispensing device, it can be arranged to have one nozzle comminuting a spray of the medicament, such as a beta-2 agonist, for example salbutamol, where the average droplet charge +/− Qa could then be accurately adjusted by arranging for deionized water to be comminuted from the second nozzle with an average charge −/+ Qb, thus the desired final value on the inhaled spray of could be Qa plus or minus Qb.

Similarly, for example, in charged droplet spraying of crops it is sometimes highly beneficial if the droplet charge can be adjusted independently of its mass, in order to achieve penetration into dense foliage.

As indicated above, various means have been used to deliver liquid to the comminution site prior to comminution generation. Most are mechanical in nature although European Patent number 0029301 discloses a spray device incorporating a pump wherein the hydrostatic pressure is generated by an electric potential between two electrodes immrosed in the feeder stream of the liquid to be sprayed. It is a further aspect of the present invention that there is provided a novel electrically powered pump, suitable for pumping liquid to the comminution site of an electrohydrodynamic comminution device.

An important component of the dispensing devices described above is the means for supplying the liquid to the commninution site. Accordingly, in a further aspect of the present invention there is provided a pump, suitable for supplying liquid to the comminution site of a comminution means, which pump comprises an electrically insulating conduit for the liquid, the conduit enclosing an electrically insulating solid permeable to liquid, means for retaining the solid within the conduit and means for applying an electric field across the solid, so that in use, when the electric field is applied, liquid is induced to flow through the solid and hence along the conduit.

The dimensions of the conduit are not considered to be limidng to the successful operation of the invention, the essential feature being the presence of an electric field across the solid.

A suitable means for applying an electric field across the solid is provided by a pair of permeable electrodes, spaced apart along the conduit.

It is preferred if the solid substantially fills the conduit. A suitable conduit is a pipe, for example a cylindrical pipe.

Conveniently, the means for applying an electric field across the solid also acts as the retaining means for the solid in the conduit.

In one suitable form of the invention a pair of permeable electrodes are fixed apart along the conduit and the permeable solid substantially fills the space defined by the electrodes and the inner wall or walls of the conduit.

Preferably, the electrodes are flat plates shaped to retain the solid within the conduit, thus when the conduit is a pipe the electrodes are disc shaped.

The permeable electrodes are conveniently constructed from wire gauze or from electrically conducting titanium oxide.

Suitably, the liquid permeable solid is in powdered form. Suitable powdered forms include powdered ceramic, powdered silica, powdered plastic and clay.

Alternatively, the liquid permeable solid may be a fibrous solid, suitably a fibrous ceramic or polymer fibres.

In addition as an alternative to powdered or fibrous forms the electrically insulating solid may be any permeable form of ceramic, silica, plastic or clay.

The relationship between flow rate, dimensions of the conduit, applied voltage and the nature of permeable solid ray helpfully be described by the equation shown in Scheme (I) which assumes that the permeable solid is formed by a bundle of parallel capillary fibres of radius 'r':

Scheme (I)

$$Flow\ rate = \frac{n\varepsilon_r\varepsilon_o\xi\pi r^2}{\eta} \cdot \frac{V}{L}\ \text{m/sec}$$

wherein:

n=number of capillaries of radius r,

V=applied voltage;

L=distance between electrodes;

$\xi$=Zeta potential;

$\varepsilon_r$=relative permittivity;

$\varepsilon_o$=permittivity of free space; and $\eta$=viscosity of the liquid.

Although Scheme (I) is considered to be useful for describing the theoretical basis for the pump of the present invention, the invention is not considered to be limited by the relationship set out in Scheme (I).

In a preferred form, when used to supply a liquid formulation in the dispensing device of the invention, the pump comprises an electrically insulating tube, a pair of electrodes permeable to liquid and fixed apart along the tube and a powdered solid permeable to liquid, the solid substantially filling the space defined by the electrodes and the inner wall of the tube and means for applying an electric field to the electrodes, so that in use, when the field is applied, liquid is induced to flow through the solid and hence along the tube.

The above described liquid supply means allows an even liquid flow at precise rates, using the same (electrical) energy source that is used to generate the droplets thus requinng no mechanical means of pressurizing the liquid. The entire unit may thus be powered by very small batteyc riven voltage sources, or even by a hand-operated piezoelectric device such as a stack of PVDF film or barium titanate ceramic. The device may thus be made pocket-sized.

The invention also extends to the conduit, retaining means and means for applying the electric field as described above for use with the solid as defined above.

When used herein 'a comminution' includes a liquid droplet spray.

When used herein 'medicament' includes proprietary medicines, pharmaceutical medicines and veterinary medicines.

When used herein, unless more specifically defined herein, 'inhaled administration' includes administration to and via the upper respiratory tract, including the nasal mucosa, and the lower respiratory tract.

When used herein 'electrically insulating' relates to a level of electrical insulation sufficient to allow an electric field to be applied across the solid, wherein the field is sufficient to induce liquid flow; preferably it includes semi and fully insulating materials When used herein the terms 'liquid permeable' or 'permeable to liquid' as applied to, for example, the solid and electrodes relate to solid and electrodes which are intrinsically permeable to liquid or to solid or electrodes which can be rendered permeable by processes for example, in the case of the solid, granulation or powdering or, for the electrode, by forming into shapes which allow the passage of liquid, such as mesh shapes.

The liquid medicinal formulations for use in the device of the invention may be formulated according to conventional procedures, such as those disclosed in the US Pharmacopoeia, the European Pharmacopoeia, 2nd Edition, Martindale The Extra Pharmacopoeia, 29th Edition, Pharmaceutical Press and the Veterinary Pharmacopoeia.

The liquid cosmetic formulations for use in the device of the invention may be formulated according to conventional procedures, such as those disclosed in Harry's Cosmeticology, 9th Edition. 1982, George Goodwin, London.

The invention may now be described, by way of example, with reference to the accompanying drawings.

COMMINUTION SITES

Figure 1:
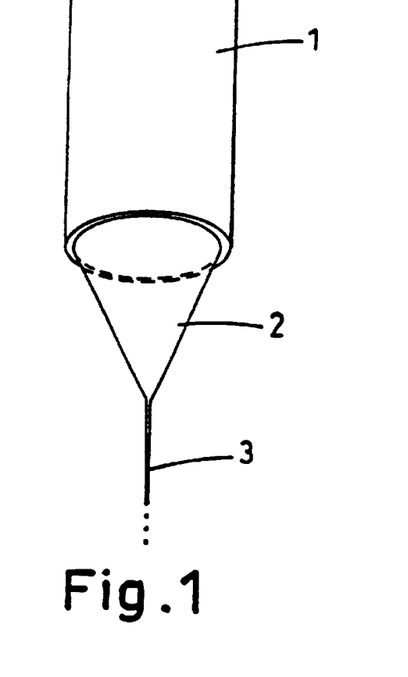
FIGS. 1 to 4 illustrate examples of comminution sites of the device of the invention.

FIG. 1 shows a thin-walled capillary tube (1), which may be made of conducting or semiconducting material and which may be electrically connected to a source of high-voltage diect-current, either directly or through the liquid. A single jet (3) is produced from a cusp (2) of liquid, both of which fom natually, according to the voltage and flow rate for a given liquid.

Figure 2:
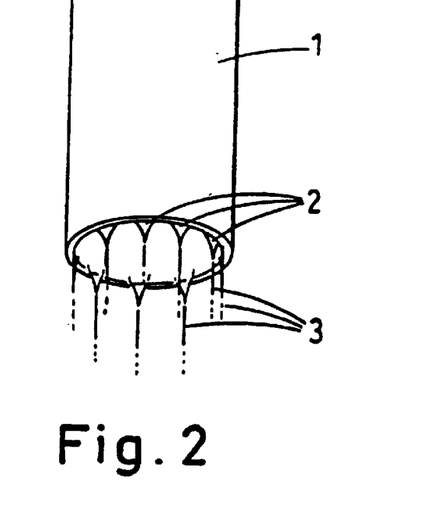

FIG. 2 shows a similar tube (1) used at a lower flow rate and voltage which are adjusted so as to produce multiple cusps (2) and jets (3) issuing from the region of the ends of the thin-walled tube (1).

Figure 3:
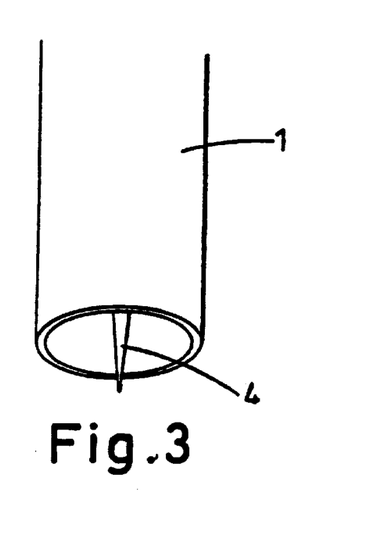

FIG. 3 shows a conducting or semiconducting cylinder (1) which may have a larger diameter than those shown in FIGS. 1 and 2. This nozzle has an inner-member, (4) which is approimately coaxial with the outer tube, (1).

Figure 4:
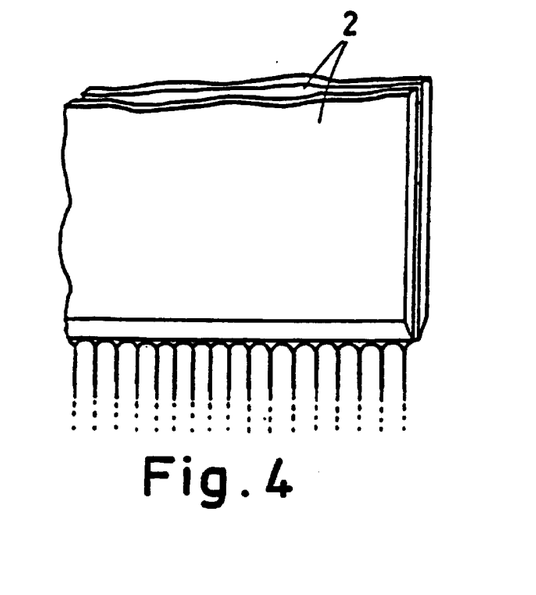

FIG. 4 shows a slot nozzle, formed between two parallel plates (2) having conducting, or semiconducting edges electrically connected to a high-voltage direct-current supply, from which the liquid emerges, forming cusps and jets when the voltage supply and liquid flow rates are suitably adjusted according to the type of liquid being sprayed. For a given jet (and thus droplet) size, and a given liquid, this nozzle may enable a higher flow rate to be achieved than those in which a single cusp and jet are used.

Figure 5:
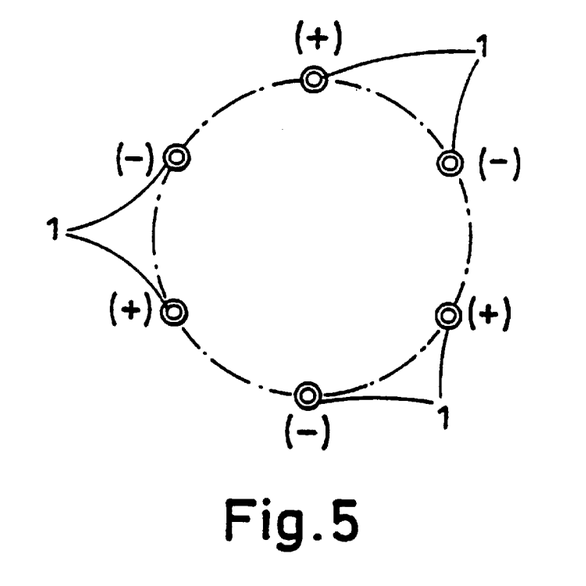
FIG. 5 is a plan view illustrating a multi-nozzle comminution site of the device of the invention.

FIG. 5, shows one example of an array of six nozzles (1) in a circular pattern, centrally mixing the sprays.

Liquid Supply Means

Figure 6:
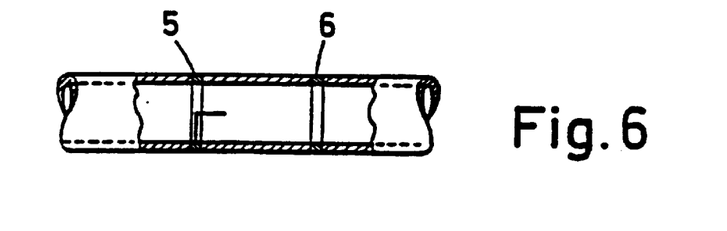
FIGS. 6 and 7 illustrate examples of the liquid supply means of the device of the invention.

An example of such a device is illustrated in FIG. 6 which shows an ion steam method. wherein a high voltage electrode (5) breaks up pairs of charge carriers within the liquid, thus neutralizing those of opposite polarity at the electrode, and leaving a large population of monionized like-polarity charge carriers which stream away from the high voltage electrode by coulQmbic force, thus moving the liquid in the direction of the counter electrode (6) by means of viscous drag. This pumping means requires that an electrode (5) is able to effectively inject like-polarity charge carriers into the liquid, close to the electrode (5). This may be effectively done by using a sharp-edged conducting or semiconducting surface, held at a sufficiently high potential to disrupt lightly bonded charge carriers or to ionize the liquid. Normally, it is only possible to establish a strong enough field for both creating unipolar charge carriers and pumping the liquid, when the liquid is of sufficient resistivity. Typically a resistivity of, say 10 (exp. 8) ohm meters, will pump at several millilitre per minute, with a head of up to one meter, at a voltage of 10 to 20 kilovolts, and a direct current of only a few microamperes. More conductive liquids will draw more current and will establish a weaker electric field. Thus highly conducting liquids, such as, say tap water may not establish a practicable drag pressure.

Figure 7:
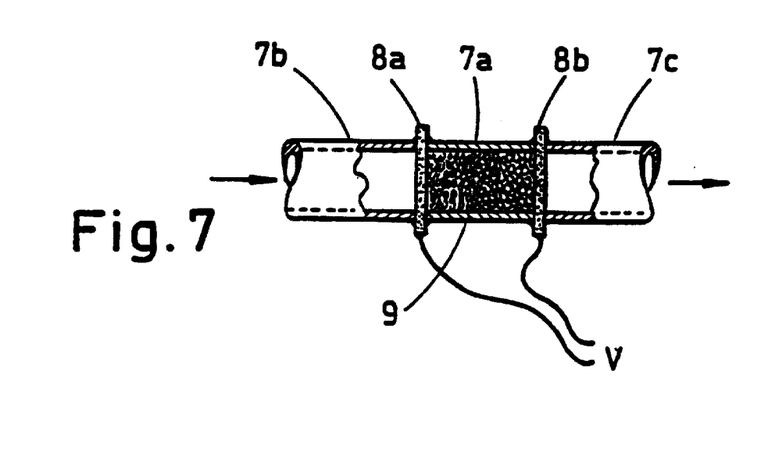

FIG. 7 shows an example of the novel pump of the invention in which a plastic tube (7a), 1.0 cm long, internal diameter 1.0 cm and 0.8 mm wall thickness has one of a pair of disc-shaped wire gauze electrodes (8a and 8b) bonded to each of its ends. A source of dc. voltage is connected to each electode. Liquid is supplied to and taken from tube (7a) by two further plastic tubes (7b and 7c) one of each being bonded to each wire gauze electrode (8a or 8b). Glass tube (7a) is filled with powdered silica (9). In operation, on applying a voltage to the electrodes (8a and 8b) a net forward force is exerted on the liquid which is interfaced with the silica (9) due to the presence of a double layer of charge at the solid-liquid interface. The polarity of the dc voltage is set so as to draw the liquid in the required direction, according to the polarity of the charge layer residing in the liquid at the liquid-solid interface. The pressure developed may be enhanced by using a solid of finer mesh size, thereby increasing n (see Scheme(I) above), with a maximized specific surface and with maximal zeta potential difference at the solid-liquid interface. Electrode voltages may be adjusted in accorahce with the length of the current path between the two electrodes, so as to liit current flow to a desired value.

Using the device illustrated in FIG. 6 a flow rate of 0.03 mL sec$^{-1}$ was obtained with mineral oil of resistivity $10^7$ ohm m, relative permitivity ~2.5 and viscosity 22 centistokes with an applied voltage of 20 kV.

Electrical Charging Means

Figure 8:
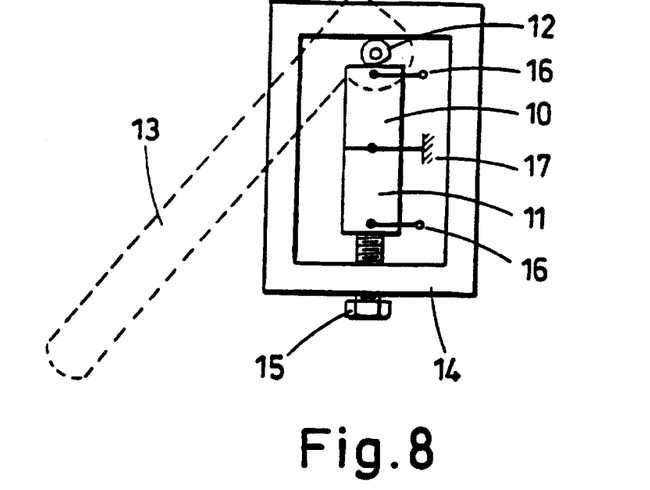
FIG. 8 is a schematic drawing illustrating an example of a charging means of the device of the invention.

An example of this isra piezo electric generator. FIG. 8 illustrates a pair of piezoelectric ceramic generators (10) (11) which may be easily squeezed by a cam (12) operated by a trigger-shaped lever (13). The entire assembly may be housed in a strong steel frame, (14), and the piezoelectric pair may be held tight by adjustment screw (15). The voltage terminals (16) are the two live electrodes for connection to the pumps and nozzles, whilst terminal (17) is earthed, say to the steel frame.

When the lever (13) is pulled inward, the two ceramic generators (10) and (11) will produce high voltages upon the terminals (16) placed at the end surfaces, which may be used to activate both the electrokinetic pumps and the nozzles.

Typical values of charge from say a barium titanate ceramic of about 1.0 cm length and 1.0 sq cm surface area would be 1.0 or 2.0 microcoulomb per squeeze, of either positive or negative polarity. Upon release of the squeezing pressure, a similar charge will flow in the opposite direction. A typical voltage would be say 5,000 to 10,000 volts. Thus, pumping and atomizing may both be achieved by hand operation of a single pair of piezoelectric generators at appropriate voltages, say 5,000 volts, and sufficient currents, say 2.0 microcoulombs per second (2.0 microamperes).

The piezoelectric material may be chosen from several types, such as barium titanate ceramic, or pvdf polymers, which generate significant high-voltage electric charge displacement upon being pressurized. The choice and capacity may be so chosen as to offer control of the degree of pumping and/or atomization when operated. The liquid flow induction, and the nozzle atomization will occur when the piezo-electric generators are squeezed, and again (with opposite polarty) when the piezoelectric generators are released from pressure. The device is arranged so that when squeezed, and when released, the pumps and nozzles will operate without alteration of flow rate or droplet size. Only polarity will change (reverse) in the two modes of operation arising from pressure and release of pressure. This will maintain constant flow and droplet generation, and mixing of species and/or charge-to-mass ratio adjustment of the sprays, during the active modes of pressure, and release of pressure.

Figure 9:
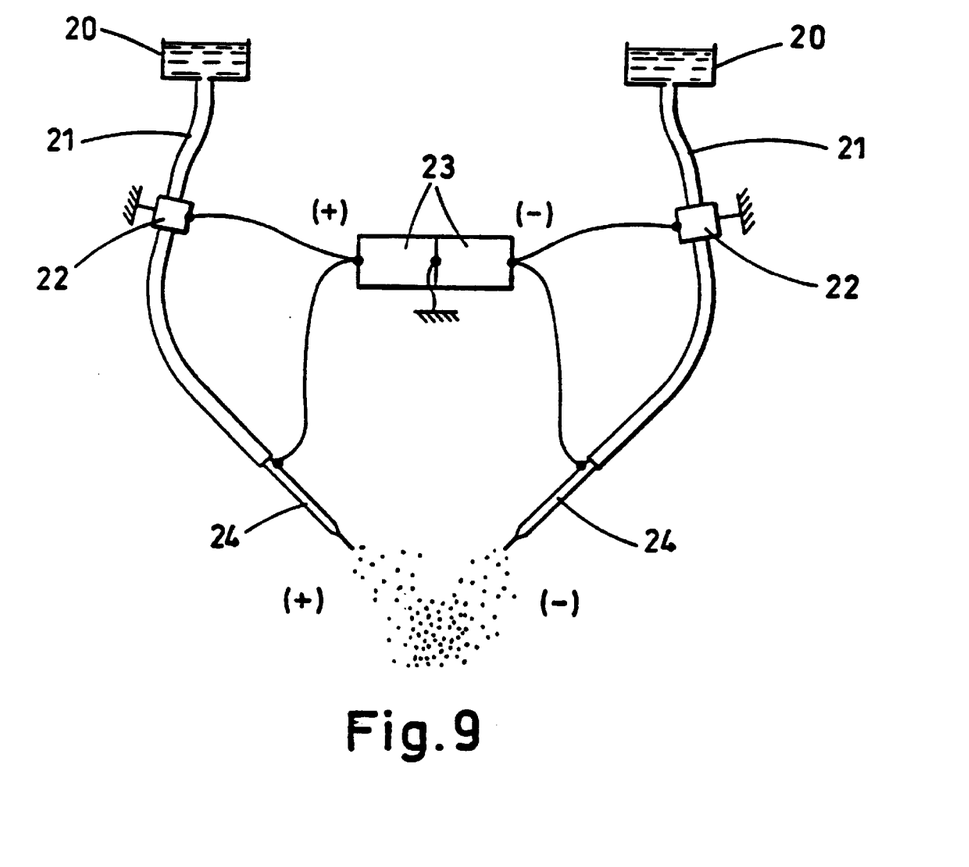
FIGS. 9 and 10 are schematic drawings each illustrating an example of a device of the invention.

Particular examples of the dispenser of the invention are illustrated below:

FIG. 9 shows a dispenser of the invention, in which liquid in each of two reservoirs (20) is caused to flow along suitable conduit, say polyethelene tubing (21) into two electrolinetic pumps (22), say by gravity feed. The two piezoelectric generators (23) are then squeezed so that a high voltage charge is induced at the two faces of the piezoelectric materials. These high voltages will then appear at the terminals of the pumps (22), which are electrically connected to the piezoelectric material by wire conductors.

At the same time, these high voltages will appear at the two conducting, or semi-conducting, capillary-tube nozzles (24). Thus, when the two liquids reach the two nozzles, the liquids will emerge from the nozzles as comminuted droplets with electrical charges of opposing polarity. The droplets will then be attracted to each other by electric field forces, and will tend to mix vigorously.

The value of droplet charge on each of the two streams of droplets may be independently adjusted to produce the optimum residual value by one or more of several means: the size, shape, and/or materials of the two piezoelectric materials may be set to give differing values of voltage and charge; the two liquid flow rates may also be adjusted, either by suitable design of the two electrokinetic pumps, or by differing values of piezoelectric voltage applied to the two pumps thus directly influencing droplet charge for a given voltage and nozzle design; and the droplet size and charge of the two liquids may be independendy adjusted by the formulations of the two liquids, especially by adjustment of the liquid resistivities.

Figure 10:
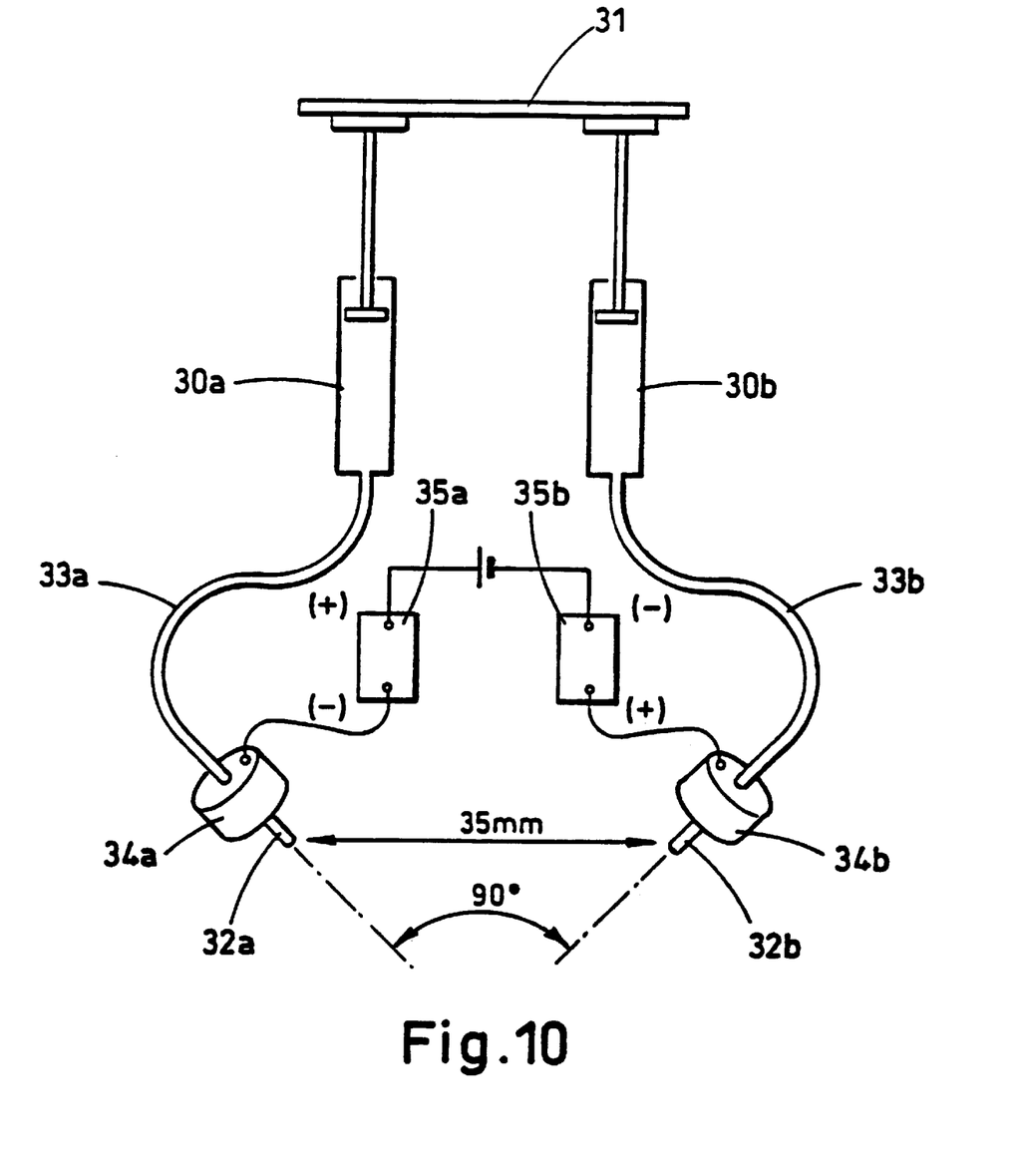

A second example of the dispenser of the invention is illustrated in FIG. 10: Two identical syringes (30a and 30b) are actuated by a rigid plate (31), the plate being attached to a motor drive unit. Two identical capillary nozzles (32a and 32b) each with internal diameters of 0.5 mm are each interconnected with one of the syringes (30a or 30b) by one of a pair of flexible tubes (33a and 33b). Each nozzle (32a and 32b) is fixed in a non-conducting mounting (34a or 34b respectively) so as to define an angle of approximately 90° with each other. One nozzle (32a) is attached to a high voltage source (35a) of (+) 6.7 kilovolts and the other nozzle (32b) is attached to a high voltage source (35b) of (−) 6.7 kilovolts.

In one particular experiment using the above described device, the flow rates of liquid (a mixture of 80% ethanol and 20% polyethylene glycol) from each syringe was adjusted to 1.0 μL/sec. The nozzles were attached to the high voltage sources of (+) and (−) 6.7 kVolts respectively. The two spray clouds were observed to mix virtually completely to provide an electrically neutral spray.

What is claimed is:

1. A device for comminuting liquid, comprising:
   a first liquid supplier having a first liquid outlet and operable to supply liquid with a resistivity in the range of $10^2$ to $10^8$ ohm meters to the first liquid outlet with a flow rate selected from 0.3 and 1.0 microliters per second;
   a second liquid supplier having a second liquid outlet and operable to supply liquid with a resistivity in the range of $10^2$ to $10^8$ ohm meters to the second liquid outlet with a flow rate of 0.3 or 1.0 microliters per second;
   a first electrohydrodynamic comminuter for subjecting liquid issuing from the first outlet to a first electrical potential to cause the liquid to be comminuted to form a first comminution;
   a second electrohydrodynamic comminuter for subjecting liquid issuing from the second outlet to a second electrical potential to cause the liquid to be comminuted to form a second comminution, wherein the first aid second electrical potentials are of opposite polarity and the first and second comminutions mix to produce droplets having a diameter in the range 0.1 to 25 micrometers.

2. A device for comminuting liquid, comprising:
   a first liquid supplier having a first liquid outlet and operable to supply liquid with a resistivity in the range of $10^2$ to $10^8$ ohm meters to the first liquid outlet with a flow rate selected from 0.3 and 1.0 microliters per second;
   a second liquid supplier having a second liquid outlet and operable to supply liquid with a resistivity in the range of $10^2$ to $10^8$ ohm meters to the second liquid outlet;
   a first electrohydrodynamic comminuter for subjecting liquid issuing from the first outlet to a first electrical potential to cause the liquid to be comminuted to form a first comminution;
   a second electrohydrodynamic comminuter for subjecting liquid issuing from the second outlet to a second electrical potential to cause the liquid to be comminuted to form a second comminution, wherein the first and second electrical potentials are of opposite polarity and the droplets of the first and second comminutions mix to produce droplets having a diameter in the range 0.5 to 10 micrometers.

3. A device for comminuting liquid, comprising:
   a first liquid supplier having a first liquid outlet;
   a second liquid supplier having a second liquid outlet;
   a first electrohydrodynamic comminuter for subjecting liquid issuing from the first outlet to an electrical potential to cause the liquid to be comminuted to form a first liquid droplet spray cloud;
   a second electrohydrodynamic comminuter for subjecting liquid issuing from the second outlet to an electrical potential to cause the liquid to be comminuted to form a second liquid droplet spray cloud; and a mixing zone for receiving the first and second spray clouds whereby substantial admixing of the droplets of the first and second spray clouds occurs in the mixing zone to produce droplets having a diameter in the range 0.5 to 10 micrometers.

4. A device according to claim 1, 2, or 3, comprising an electrical potential regulator for regulating the charge on the mixed comminution so that the mixed comminution has a net charge other than zero.

5. A device according to claims 1, 2, or 3, having means for regulating the flow rate of liquid.

6. A device according to claim 1, 2, or 3, wherein the first and second electrical potentials are such that the mixed comminution has an overall charge.

7. A medicament delivery device comprising:

a first liquid reservoir containing a medicament;

a second liquid reservoir contaiaing deioinsed water;

a first liquid supply pipe coupled to the first liquid reservoir;

a second liquid supply pipe coupled to the second liquid reservoir;

a first electrohydrodynamic comminuter for subjecting liquid issuing from the first outlet to a first electrical potential to provide a first comminution with an average charge of +/− Qa; and a second electrohydrodynamic comminuter for subjecting liquid issuing from the second outlet to a second electrical potential to provide a second comminution with an average charge of −/+ Qb which mixes with the first comminution to provide a mixed comminution having an overall net value of (Qa−Qb).

8. A medicament delivery device comprising:

a first liquid reservoir containing a medicament comprising a beta-2 agonist;

a second liquid reservoir containing an inert carrier liquid;

a first liquid supply pipe coupled to the first liquid reservoir;

a second liquid supply pipe coupled to the second liquid reservoir;

a first electrohydrodynamic comminuter for subjecting liquid issuing from the first outlet to a first electrical potential to provide a first droplet spray; and a second electrohydrodynamic comminuter for subjecting liquid issuing from the second outlet to a second electrical potential of opposite polarity to the first electrical potential to provide a second droplet spray, the first and second droplet sprays being such that the first and second droplet sprays mix to provide droplets having a diameter in the range 0.1 to 10 micrometers.

9. An inhaler comprising;

a first liquid supplier having a first liquid outlet;

a second liquid supplier having a second liquid outlet;

a first electrohydrodyamic comminuter for subjecting liquid issuing from the first outlet to an electrical potential to cause the liquid to be comminuted to form a first comminution;

a second electrohydrodynamic comminuter for subjecting liquid issuing from the second outlet to an electrical potential to cause the liquid to be comminuted to form a second comminution, the first and second outlets being angled towards one another so as to direct the first and second comminutions towards one another to cause substantial admixing of the first and second comminutions to produce droplets having a diameter in the range 0.1 to 10 micrometers.

10. A method of providing droplets for delivery to the respiratory tract, which method comprises:

supplying liquid along a first pipe to a first outlet for directing liquid into a mixing zone;

supplying liquid along a second pipe to a second outlet for directing liquid into the mixing zone;

subjecting liquid issuing from the first outlet to a first electrical potential causing the liquid to form a first comminution of droplets of one polarity; and subjecting liquid issuing from the second outlet to a second electrical potential causing the liquid to form a second comminution of droplets of a polarity opposite to the one polarity which droplets mix in the mixing zone with the droplets of the first comminution to form a mixed comminution having droplets with diameters in the range of from about 10 micrometers to 20 micrometers which is delivered to the respiratory tract.

11. An inhaler comprising:

a first reservoir for liquid;

a first pipe coupled to the first reservoir and having a first outlet;

a second reservoir for liquid;

a second pipe coupled to the second reservoir and having a second outlet;

a first electrohydrodynamic comminuter for subjecting liquid issuing from the first outlet to an electrical potential to cause the liquid to form a first comminution of one polarity;

a second electrohydrodynamic comminuter for causing liquid issuing fromn the second outlet to form a second comminution of a polarity opposite to the one polarity; and a mixing zone into which the first and second comminutions are directed whereby a mixed comminution comprising droplets having a diameter in the range 0.1 to 25 micrometers for delivery to the respiratory tract of a user is formed.

12. A pocket-sized dispenser comprising means for supplying liquid to first and second outlets; a first electrohydrodynamic comminution means for subjecting liquid issuing from the first outlet to an electrical potential to cause the liquid to be comminuted to form a comminution of one polarity; and a second electrohydrodynamic comminution means for subjecting liquid issuing from the second outlet to an electrical potential to cause the liquid to be comminuted to form a comminution of the opposite polarity, the first and second electrohydrodynamic comminution means therefore giving rise to formation of two opposite polarity comminutions and being arranged so as to cause substantial admixing of the two opposite polarity comminutions to produce droplets having a diameter in the range 0.1 to 25 micrometers.

13. A method of mixing liquids by droplet coalscence, which method comprises:

supplying liquid containing a first chemical to a first liquid outlet;

supplying liquid containing a second chemical to a second liquid outlet;

subjecting liquid issuing from the first outlet to a first electrical potential causing the liquid to form a first comminution of droplets of one polarity; and subjecting liquid issuing from the second outlet to a second electrical potential causing the liquid to form a second comminution of droplets of a polarity opposite to the one polarity whereby the opposite polarity comminutions mix and the first and second chemicals of the oppositely charged droplets chemically react upon mixing of the opposite polarity comminution to produce chemically reactive droplets having a diameter in the range 0.1 to 25 micrometers.

14. A method according to claim 13, which comprises controlling the rate of flow of liquid and the electrical potentials so as to provide droplets having a diameter in the range 0.5 to 1.0 micrometers.

15. A method according to claim 13, which comprises controlling the rate of flow of liquid and the electrical potentials to provide droplets having a diameter in the ranqe of 10 to 20 micrometers.

16. A device for comminuting liquid, comprising:
   a first liquid supplier having a first liquid outlet and operable to supply liquid with a flow rate selected from 0.3 and 1.0 microliters per second;
   a second liquid supplier having a second liquid outlet and operable to supply liquid with a flow rate of 0.3 or 1.0 microliters per second;
   a first electrohydrodynamic comminuter for subjecting liquid issuing from the first outlet to a first electrical potential to cause the liquid to be comminuted to form a first comminution;
   a second electrohydrodynamic comminuter for subjecting liquid issuing from the second outlet to a second electrical potential to cause the liquid to be comminuted to form a second comminution, wherein the first and second electrical potentials are of opposite polarity and the first and second comminutions mix to produce droplets having a diameter in the range 0.1 to 25 micrometers.

17. A device for comminuting liquid, comprising:
   a first liquid supplier having a first liquid outlet and operable to supply liquid with a flow rate selected from 0.3 and 1.0 microliters per second;
   a second liquid supplier having a second liquid outlet;
   a first electrohydrodynamic comminuter for subjecting liquid issuing from the first outlet to a first electrical potential to cause the liquid to be comminuted to form a first comminution;
   a second electrohydrodynamic comminuter for subjecting liquid issuing from the second outlet to a second electrical potential to cause the liquid to be comminuted to form a second comminution, wherein the first and second electrical potentials are of opposite polarity and the droplets of the first and second comminutions mix to produce droplets having a diameter in the range 0.5 to 10 micrometers.

18. An inhaler for enabling inhaled delivery of a therapeutic agent to the upper respiratory tract including the nasal mucosa, the inhaler comprising:
   a liquid supplier having a liquid outlet and being arranged to provide a supply liquid comprising the therapeutic agent to the liquid outlet;
   a voltage supplier for applying a high voltage directly to the liquid outlet to cause comminution of liquid issuing from the liquid outlet to produce electrically charged droplets comprising the therapeutic agent; and
   a controller for adjusting the electrical charge of the droplets to control the charge on droplets delivered to the upper respiratory tract to enable supply of the therapeutic agent to specific airways.

19. An inhaler according to claim 18, wherein the controller comprises:
   a further liquid supplier having a further liquid outlet and being arranged to provide a further liquid to the further liquid outlet;
   a further voltage supplier for applying directly to the further liquid outlet a further high voltage of opposite polarity to said high voltage to cause comminution of further liquid issuing from the further liquid outlet to produce electrically charged further droplets which have an electrical charge of the opposite polarity to the droplets comprising the therapeutic agent and which admix with said droplets comprising the therapeutic agent to produce electrically charged output droplets comprising the therapeutic agent and having an electric charge determined by the electrical charge on the droplets and the further droplets.

* * * * *

UNITED STATES PATENT AND TRADEMARK OFFICE
CERTIFICATE OF CORRECTION

PATENT NO.   : 6,318,640 B1  Page 1 of 1
DATED        : November 20, 2001
INVENTOR(S)  : Ronald Alan Coffee It is certified that error appears in the above-identified patent and that said Letters Patent is hereby corrected as shown below:

Column 10,
Line 24, change "aid" to -- and --.

Column 12,
Line 13, change "fromn" to -- from --

Signed and Sealed this

Eleventh Day of June, 2002

Attest:

Attesting Officer

JAMES E. ROGAN
Director of the United States Patent and Trademark Office